United States Patent [19]

MacMahon

[11] Patent Number: 4,752,948
[45] Date of Patent: Jun. 21, 1988

[54] MOBILE RADIOGRAPHY ALIGNMENT DEVICE

[75] Inventor: Heber MacMahon, Chicago, Ill.

[73] Assignee: University of Chicago, Chicago, Ill.

[21] Appl. No.: 936,192

[22] Filed: Dec. 1, 1986

[51] Int. Cl.$^4$ .......................... H05G 1/02; A61B 6/08; G03B 42/02

[52] U.S. Cl. .................................... 378/198; 378/205; 378/197; 378/204; 378/193

[58] Field of Search .............. 378/193, 195, 196, 197, 378/198, 181, 174, 204, 205, 186, 207

[56] References Cited

U.S. PATENT DOCUMENTS

| | | | |
|---|---|---|---|
| 2,111,903 | 2/1936 | Rona | 378/205 |
| 2,355,066 | 4/1941 | Goldfield et al. | 378/198 |
| 3,705,984 | 12/1972 | Westenberger . | |
| 3,979,595 | 9/1976 | Merchant . | |
| 4,092,544 | 5/1978 | Grim . | |
| 4,246,486 | 1/1981 | Madsen . | |
| 4,380,087 | 4/1983 | Tanaka | 378/186 |
| 4,455,672 | 6/1984 | Hahn et al. | 378/181 |
| 4,563,586 | 1/1986 | Jordan | 250/374 |

*Primary Examiner*—Carolyn E. Fields
*Assistant Examiner*—Joseph A. Hynds
*Attorney, Agent, or Firm*—Leydig, Voit & Mayer

[57] ABSTRACT

An alignment device for use in mobile radiography. In contrast to prior practice in which a film cassette is placed on one side of the patient, an x-ray source on the other, and it is left to the skill of the technician to approximate the necessary alignment, the present invention assures consistent alignment much more precise than is typically achieved. The precise alignment allows regular use of a grid in mobile radiography which helps to prevent image deterioration caused by scattered radiation. The precise alignment is achieved by providing an adaptable physical connection which when in the deployed condition, accurately establishes both the distance between the focal spot and the film plane and the alignment of the grid with respect to the central ray.

16 Claims, 5 Drawing Sheets

MOBILE RADIOGRAPHY ALIGNMENT DEVICE

BACKGROUND OF THE INVENTION

The present invention relates generally to mobile radiography, and more particularly, to means for improving the quality of images taken with mobile radiographic equipment.

In conventional hospital and nursing home practice, it is often necessary to take x-rays of patients who are confined to bed, for example, due to injury, or who are confined to the room, for example, due to contagious disease. In such instances, when the patient cannot be taken to a large fixed x-ray machine, mobile x-ray devices are brought to the patient. Radiographs taken at the bedside, however, are generally found to be inferior to those taken on the fixed apparatus in the x-ray department. In the latter, the equipment is fixed on tracks or the like so that alignment of the x-ray source, the patient and the cassette assembly can be precisely controlled. However, in the mobile x-ray situation, the x-ray source is carried on a movable trolley and the x-ray tube itself is essentially mounted on a universal joint so that it can be positioned in whatever attitude is needed to radiograph the desired portion of the anatomy of the bedridden patient. The film cassette, which carries the x-ray film, is then positioned on the side of the patient opposite to the x-ray source, and roughly in alignment with the source. It is typically held in position by whatever expedient is available; sliding it between the patient and the bed or pillow, propping it against the patient, and taping it to the rails of the bed are some examples. It will be appreciated that in that environment, alignment is usually less than precise.

In radiology in general, image sharpness and contrast of radiographs are seriously compromised by scattered radiation. This problem is controlled by the use of a grid. To deal with the scatter problem, this grid is interposed between the x-ray source and the film cassette. The grid can be a portion of a separate grid cassette into which the film cassette is inserted or alternatively installed independently but in front of the film cassette. Usually the grid is focused to the system focus-film distance, i.e., the distance between the focal spot of the x-ray source and the plane of the x-ray film. The purpose of the grid is to block scattered radiation from impinging on the film, allowing only radiation emanating directly from the focal spot to impinge on the film. The grid can be conceptualized as consisting of fine lead foil slats spaced at regular intervals in an arrangement analogous to a Venetian blind; the slats are focused at the focal distance, such as 40 inches, so that they are not perfectly parallel, but are "aimed" at the focal spot of the x-ray source. As a result, when using a grid, alignment becomes extremely significant. First of all, the proper focal distance must be maintained since the grid is focused on a spot which is a predetermined distance away. Secondly, alignment of the grid with respect to the central beam (i.e., the beam point which is normal to the grid) is essential, as can be readily appreciated when using a focused arrangement. Unfortunately in mobile radiography, such precise alignment is seldom achieved. When the grid is incorrectly positioned, "grid cut-off" results, i.e., the primary beam which should have impinged on the x-ray film is absorbed instead by the grid because it is improperly positioned.

As a consequence of these problems, many x-ray departments forego use of the grid in mobile radiography. The result is a consistently mediocre x-ray image. Those who use the grid, but align it by "eyeball technique", have the advantage of achieving improved images from time to time, but when misalignment occurs, which is often the case, achieving significantly inferior images.

The critical alignment necessary for use of a grid is achieved in fixed radiography by virtue of either a mechanical connection between the grid and the x-ray source, or an accurate light beam alignment system. However, in bedside radiography, where the x-ray tube is typically positioned at almost any angle in order to obtain a radiograph of a patient in bed, alignment of the grid becomes a significant problem.

Typically, an independent grid cassette is positioned beneath or next to the patient and the x-ray beam is directed at the patient in the general direction of the cassette. Unfortunately, placing the cassette between the patient and the patient support such as the pillow/bed makes it is very difficult to accurately align the grid cassette so that it is perpendicular to the x-ray beam.

To address the problem, some hospitals use a low ratio grid which requires less critical alignment, but which results in additional scatter impinging on the x-ray film which reduces the image quality. Even with a low ratio grid, if the grid is misaligned the image deteriorates. The conventional solution of removing the grid altogether prevents the obtaining of quality images because scattered radiation is not blocked from the film. When a grid is used, varying amounts of grid cut-off and variations in tube film distance cause the density of sequential radiographs to vary from one day to the next. This leads to difficulty in diagnosis. This grid cut-off effect often requires the repetition of the taking of the radiograph which brings about not only increased film consumption, and a waste of hospital personnel, but also an increased patient dosage of radiation.

In the x-ray department, accurate grid alignment and focal distance determination is achieved by mechanical and/or visual alignment devices. In mobile radiography, visual methods exist for focal distance determination but several problems make visual determinations difficult and impractical to use. Such devices do not solve the problem, but only serve as an aid for the technician. Since the grid cassette is normally placed between the patient and the bed, the grid cassette is largely obscured from sight by the patient's body, thus rendering the use of visual light beams very difficult. Because of this difficulty, beam alignment and focal distance determination is achieved by an "eyeballing technique" which inevitably varies the results. The distance can be measured with a tape, though in practice, it too, is often eyeballed.

Due to these limitations, the use of grids in bedside radiography is seriously limited. Because of these manual alignment problems, many hospitals will forego the grid entirely and accept the poor image quality.

At present, it is difficult to use mobile radiography to obtain either a horizontal beam for upright chest and abdominal exams or for decubitus views. Such views are difficult to obtain because the grid cassette must be propped or taped in position, again creating alignment problems. Alternatively, a separate mobile grid support device can be used, though this is not widely utilized for practical reasons. A horizontal view is highly desirable in radiography because when the patient stands or sits erect between the film and the x-ray device, air-fluid levels or abnormal air collections can be clearly demonstrated, though such findings might be invisible with a vertical or semi-vertical beam.

SUMMARY OF THE INVENTION

It is an aim of the present invention to approach the image quality of fixed x-ray apparatus using mobile x-ray equipment.

In accomplishing that aim, it is an object of the present invention to allow use of a grid in connection with an x-ray cassette used in mobile radiography and to consistently align the x-ray beam with the grid.

A more specific object is to provide, in connection with mobile radiography, means for insuring accurate alignment of a grid cassette with the focal spot of an associated x-ray tube, no matter what position the tube might be in in performing a bedside x-ray examination.

BRIEF DESCRIPTION OF THE DRAWINGS

Other objects and advantages of the invention will become apparent upon reading the following detailed description and upon reference to the drawings, in which.

Figure 1:
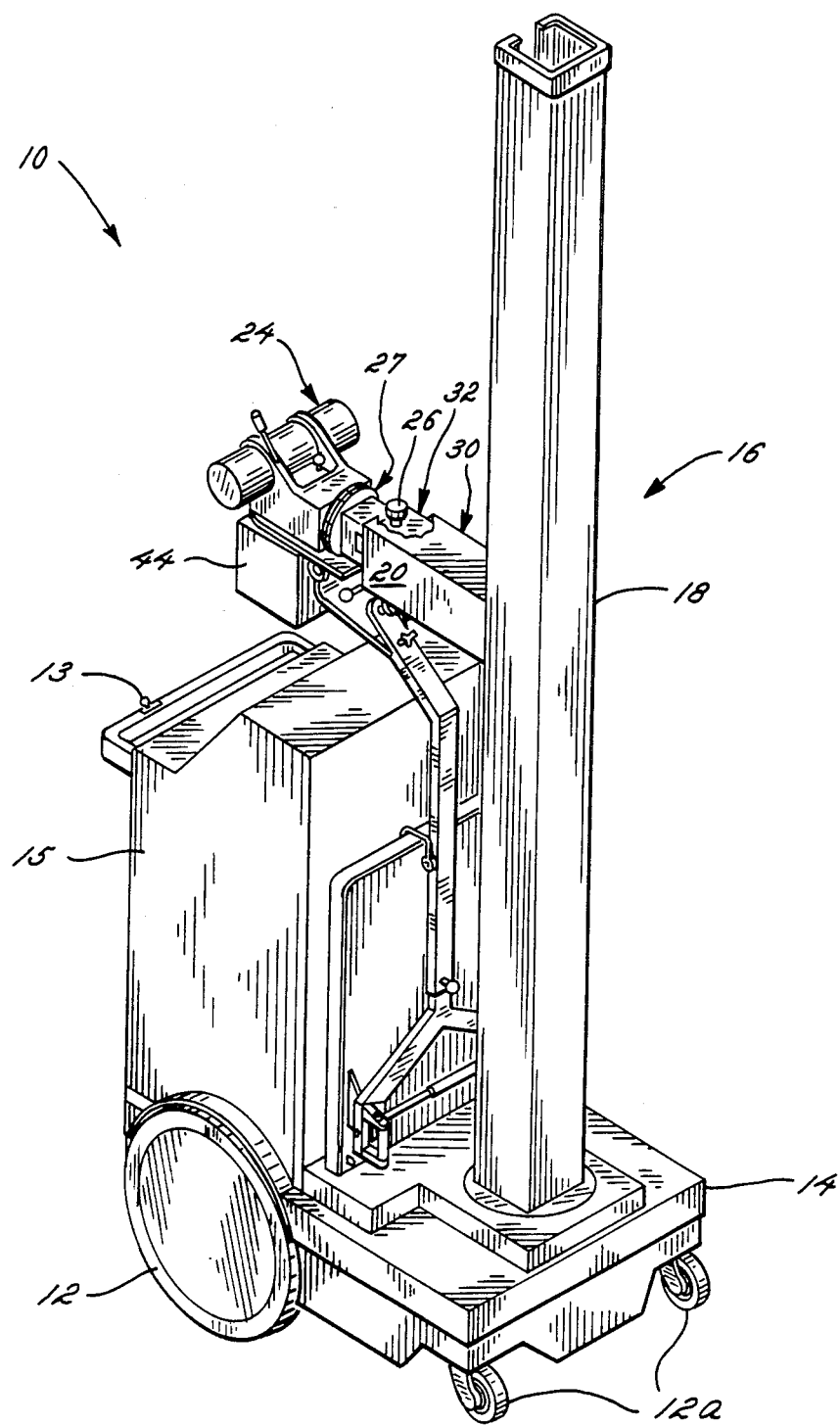
FIG. 1 is a schematic view, in perspective showing a mobile radiographic device incorporating a film positioning device constructed in accordance with the present invention and shown in the closed or "transport" position.

While the invention is susceptible of various modifications and alternative constructions, certain illustrated embodiments thereof have been shown in the drawings and will be described below in detail. It should be understood, however, that there is no intention to limit the invention to the specific forms disclosed, but on the contrary, the intention is to cover all modifications, alternative constructions and equivalents falling within the spirit and scope of the invention.

DETAILED DESCRIPTION

Turning now to the drawings, FIG. 1 is a perspective view of a typical mobile radiographic device incorporating apparatus for improving the quality of the radiographic image constructed in accordance with the present invention. It is pointed out with respect to the mobile x-ray machine itself that the illustration is partly schematic and simplified, e.g., details of certain mechanisms are not shown, high voltage cables are eliminated, etc. Sufficient detail is given to understand the structure and operation of the present invention.

The mobile radiographic device 10 is constructed as compactly as possible in order to allow access to the bed in a typical hospital room or ward, while at the same time carrying a relatively heavy x-ray tube which must be positioned in any of numerous orientations in order to produce radiographs of patients who are confined to bed. The mobile radiographic apparatus 10 is supported on wheels 12, 12a, wheels 12a being pivotable for steering and wheels 12 being power driven for transport of the device from the radiographic department to the hospital room where the radiographs are to be taken. A switch 13 controls the power drive (not shown) which is used to transport the device to the location where it is to be utilized.

Supported on the wheels is a platform 14 which carries the radiographic apparatus generally indicated at 10 including a generator and control system 15, a multi-position x-ray tube support generally indicated at 16, and an x-ray source generally indicated at 24 and held by the support 16.

The support 16 generally comprises a vertical standard 18 which carries a telescoping arm 20 to which the x-ray source 24 is ultimately attached. The telescoping arm 20 is movable upwardly and downwardly on the standard 18 and a counterbalance mechanism (not shown) is provided for ease of raising and lowering the equipment carried by the standard 18. As is conventional, locking means is provided to secure the telescoping arm 20 in place on the standard 18 when a desired position is achieved.

The standard 18 itself is pivotable on the platform 14 by means of a bearing structure mounted in the platform and holding the standard 18 for rotation about a vertical axis. Typically a friction brake associated with the bearing support provides sufficient restraint to hold the column in any position to which it is pivoted. A full 360° of rotation allows the patient to be approached from either side of the bed. The telescoping arm 20 comprises at least two sections 30, 32 and allows the distance between the supporting standard 18 and the x-ray source 24 to be adjusted at will. Conventional locks can also be provided for securing the arm in a desired position.

By the means thus far described, the x-ray source 24 can be moved to virtually any position in the area of a bedside. Means are also provided for rotating the x-ray source 24 such that it can assume numerous attitudes with respect to the patient to radiograph the necessary portion or portions of the anatomy at the proper angle. To that end, there is provided a first rotation lock 26 securing the x-ray source 24 to the telescoping arm 16 and allowing the tube to pivot in a horizontal plane about a vertical pivoting axis at the center of locking hinge 26. Similarly, the x-ray source 24 is secured via the hinge 26 to the telescoping arm 16 via a horizontal rotation device 27 also having a lock, which allows the source 24 to pivot in a vertical plane about a center line defined between the centers of the vertical and horizontal rotation devices.

It will be noted that certain of the aforementioned adjustments are depicted in relatively schematic form since they are available on commercially available x-ray devices and are well known to those working in this art. However, it will also be reiterated that while the device allows the tube to be moved through numerous positions, typically x-rays are taken at only certain of those because of the difficulty of alignment of the source and x-ray film. And even when it is possible to support the film cassette with respect to the patient such that the degree of maneuverability of the x-ray tube can be taken advantage of, severe alignment problems present themselves, discussed in the introduction, which prevent the obtaining of consistently high quality x-ray images.

In contrast to fixed radiography where the x-ray source and film are both vertical and the patient is disposed therebetween, or where the patient is prone on a table and the x-ray source and film are aligned for vertical operation, bedside radiography poses many additional problems. The patient may be slightly reclined, erect, or prone, and the x-ray source must pivot through whatever degrees of motion are necessary not only to compensate for the bed, or support on which the patient is lying, but also to focus, more or less, at the film lying behind the patient, often between the patient's back and the bed or a pillow.

In accordance with the invention, there is provided means, in a mobile x-ray environment, for assuring precise and repeatable alignment and positioning between the x-ray source aimed at the patient, and the film/cassette positioned to record the information required by the radiologist.

Figure 2:
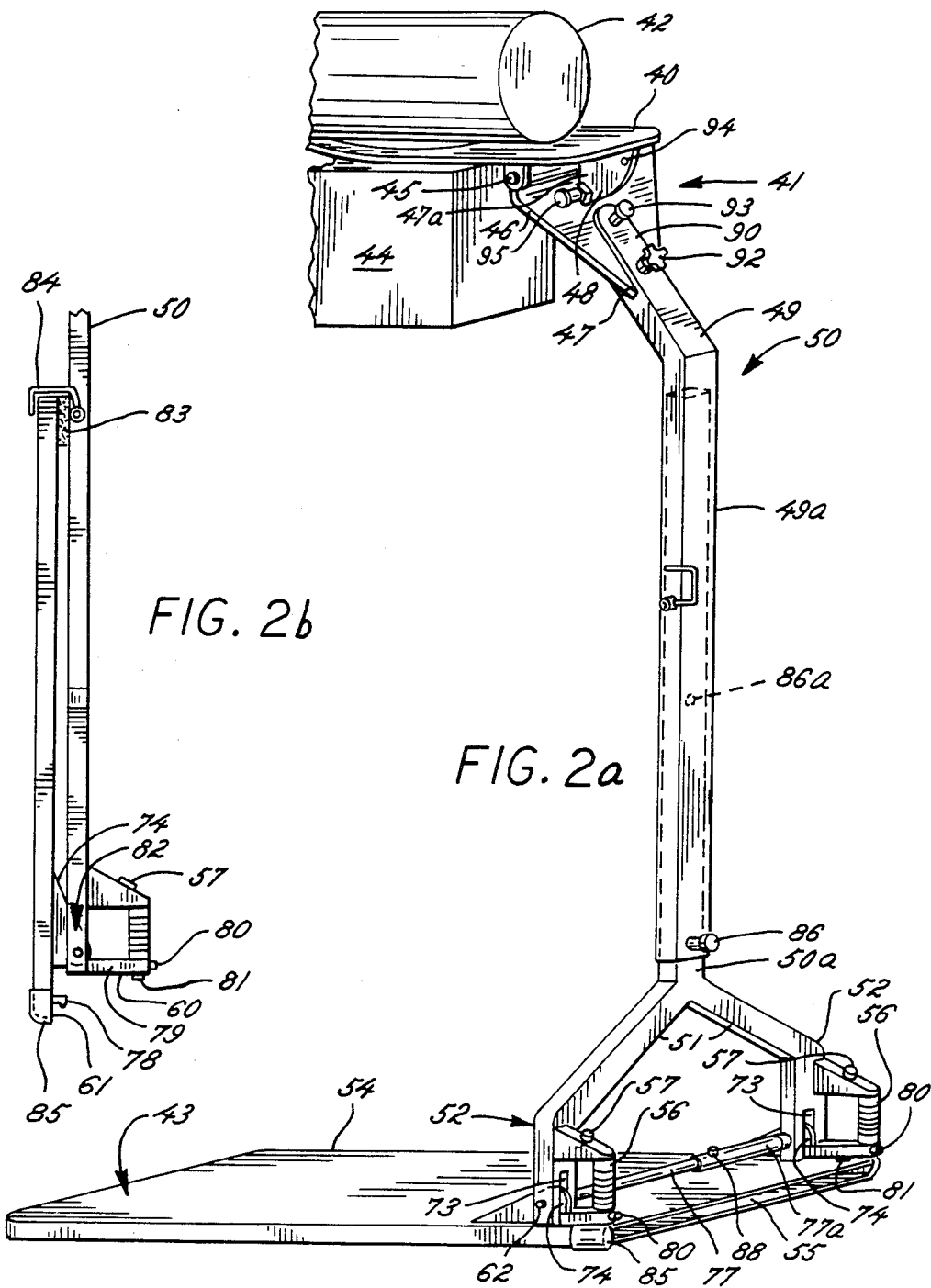
FIGS. 2a and 2b are perspective views of the folding cassette holder of FIG. 1 in the deployed and closed position, respectively.

One embodiment of the invention is shown deployed in an operative position in FIG. 2a (and shown in the traveling or transport position in FIGS. 1 and 2b). In practicing the invention, mounting means are associated with the x-ray generator schematically illustrated at 42 and its associated collimator 44. The mounting means, generally illustrated at 41, is adapted, when deployed, to establish a plane 43 which is as a first requirement positioned precisely at the focal distance from the x-ray focal spot, and as a second requirement aligned in a horizontal direction such that the film is accurately positioned with respect to the collimated beam and the central ray is accurately positioned with respect to the grid.

In greater detail, mounting means, shown in the drawings in the form of a plate 40 are interposed between the x-ray tube schematically illustrated at 42 and the collimator 44. It is well known that the collimator 44 is utilized to tailor the profile of the x-ray beam such that only the area of the body which it is desired to examine is exposed to x-rays, thus limiting the x-ray dose. Typically, the collimator 44 is attached to the plate 40 in a fixed relationship, but the plate 40 with attached collimator 44 is rotatable about the center line of the collimator 44. This provides at least one benefit, namely, yet another degree of freedom for the x-ray source 42 and associated film cassette in that the collimator 44 can be rotated about its center to rotate the square or rectangular beam about that center.

The mounting means 40 is provided with means for accepting a pin 45 adapted to rotatably mount a yoke 46 about the axis of the pin 45. The yoke has a central aperture 47a which slidably receives an arcuate detented stop 48 securely fixed with respect to the mounting plate 40. The mounting plate 40 has a fixed rearward stop so that its lowermost position is as illustrated in the drawings. Extending from an angled portion 47 of the yoke 46 is a mounting arm 50 of precise dimension, which includes an offset portion 49 and a depending portion 49a. The offset serves to provide sufficient clearance to accommodate portions of the patient's body which are not to be radiographed when taking certain views. The depending portion 49a Y's into a pair of arms 51 terminating in a pair of sections 52 which in the preferred embodiment are perpendicular to the mounting plate 40. The aforementioned plane 43 is established by a cassette carrier 54 having an open end for receiving a cassette drawer 55 which slides within the carrier from the rear (at the right as shown in FIG. 2a). As will be described below, in the illustrated embodiment, the cassette carrier 54 contains the focused grid whereas the cassette drawer 55 contains the film cassette which in turn contains the x-ray film and associated image intensifiers.

As a feature of the invention, handles 56 are provided near the lower end of the arms 52. These allow convenient access for the technician to maneuver the cassette holder after the x-ray tube is first approximately positioned. Lock switches 57, positioned so that they can be actuated by the thumb while the technician's hand engage a handle 56, are connected to the mechanism which locks the vertical position of the telescoping arm 20 on the standard 18 both to facilitate positioning of the cassette and to prevent accidental lowering of the x-ray source 42 onto the patient.

The cassette carrier 54 may be formed of a steel or alloy frame having an upper surface 48 and a corresponding lower surface of durable and readily cleanable plastic material such as that sold under the trademark Teflon.

Means are provided for assuring that in the deployed condition illustrated in FIG. 2a surface 43 is parallel to the mounting plate 40, the grid carried in the carrier 54 is aligned with the central beam from the focal spot of the x-ray source 42, and the plane of the film within the cassette drawer 55 is at the specified focal distance from the x-ray source 42.

In the embodiment, illustrated in FIGS. 2a and 2b such means are implemented by a pair of mating surfaces 60, 61 which operate in conjunction with pivot point 62 to establish a precise and aligned relationship between the surface 43 and the x-ray source 42. It is preferred that the depending arms 50 be perpendicularly disposed with respect to the plate 40 whereupon the surfaces 60, 61 are disposed to establish a right angle when the cassette holder is in the deployed position. In the illustrated embodiment, the handles 56 are conveniently formed with buttresses to form the surface 60 whereas the surface 61 is a continuation of the surface 48. The hinge point 62 is located to appropriately establish the desired right-angle relationship.

In order to form the hinge point 62, the lower portions of the arms 52 facing the cassette carrier 54 are cut away to form a pair of clevices 73 as illustrated in FIG. 2a. The cassette carrier 54, in turn, has a pair of gussets 74 smoothly faring into the metal frame of the carrier 54. Mating apertures are formed in the gussets at 74 and in the clevice at 73 to receive a mounting axle 77 about which the carrier 54 can pivot. Preferably, the apertures 73, 74 are fitted with bushings which accurately establish the position of the axle 77 and therefore the position of the carrier 54 with respect to the x-ray tube. In order to avoid pinch points, it is desirable that the axle 77 not extend beyond the bushing mounted in the exterior clevice aperture in each of the arms 52.

Since the x-ray tube with attached cassette positioning apparatus can be positioned in numerous attitudes, it is desirable that means be provided for locking the cassette holder in its fixed 90° position during operation. To that end, the lower end of the carrier 54 is provided with a catch 78 and the buttress surface of each handle is provided with an aperture at 79 which mates the catch and allows it to cooperate with a release 80. When the carrier 54 is lowered to its operative or deployed position, the catch 78 protrudes through the aperture 79 and is engaged by the release 80. When it is desired to return the carrier 54 to its inoperative position, a release button 81 is depressed which releases the catch 78 and allows the carrier 54 to be swung to its vertical position. A pair of coil springs 82 are provided to assist the carrier 54 into its upward position and padding 83 is provided on the inside of the arm 50 to cushion the impact should the carrier 54 raise too quickly. A transport lock 84 is also conveniently provided. For protection of the cassette carrier, a nylon bearing surface 85 is provided at the edge which bears against the platform 14 in the transport position.

As a further feature of the device, means are provided for altering the focal distance of the apparatus so as to accommodate a wider variety of procedures. For example, in certain procedures such as lateral chest views, a 40" focal length can produce excessive magnification. That can be corrected by increasing the focus-film distance. In the illustrated embodiment, that is achieved by constructing arm 50 as a telescoping arm held in the normal position, such as 40" focal length by means of a detent 86. When it is desired to increase the focal length of the apparatus, the detent 86 is released and arm portion 50a withdrawn from surrounding arm portion 49a until a second detent position 86a is engaged to establish the second focal length. An example of the second focal length can be 56" which is easily accommodated by the illustrated apparatus and which can significantly serve to reduce the excessive magnification problem described above. An example of such a procedure might be when a patient who is mobile but confined to room because of contagious disease but requires chest x-rays. He cannot be transported to the x-ray department, so the mobile apparatus must come to him. If a series of chest x-rays is desired, it is useful to increase the focal length, and the above-described feature allows that. Of course, when the focal length is increased, the grid in the apparatus must also be changed to accommodate the new focal length. Alternatively, a different cassette holder or a grid cassette with a grid of appropriate feral length may be employed.

As a further feature of the invention, it may be desirable in certain situations to remove the entire positioning apparatus (with the exception of course of the mounting parts), or simply to remove the cassette from the arm 50. Such situations may occur, for example, when the patient, perhaps in traction, presents such an awkward situation it is difficult without causing undue discomfort to position the fixed apparatus. In other situations, it may be easier to position the cassette holder beneath the patient free of the arm 50, following which the arm 50 can be reattached, or at least used as a guide for setting distance and alignment of the x-ray source 42.

To accomplish the aim of removing the cassette while leaving the arm in position, the axle 77 is made of two concentric pieces, axially displaceable with respect to each other and held in position by a detent 88. When it is desired to release the cassette from the arm 50, the detent 88 is depressed, and the axle portions 77, 77a moved axially apart until they separate. The axle portions 77, 77a are then withdrawn from the bushings forming the hinge, freeing the cassette from the arm 50.

The cassette can then be located in position for the view to be taken, and the arm 50 either reattached, or used as a guide to finally position the x-ray source before making the exposure.

For removing the entire holder from the x-ray machine, the arm 50 at its inclined portion 49a is provided with a clevice 90 mating a mounting tongue 47 of the yoke 46. A threaded fastener 92 secures the arm to the tongue portion of the yoke. A detent 93 simply serves to maintain the axial alignment between the arm 50 and the yoke. Thus, when it is desired to quickly release the entire positioning device from the x-ray machine, it is simply a matter of releasing the fastener 92 and detent 93, and dropping the entire apparatus away.

As a further convenience in positioning the fixed geometry cassette holder with respect to a patient, the arcuate plate has an additional detent position 94 and an associated detent 95 which allows the arm and attached cassette to be rotated away from the operating position. Thus, in some circumstances, it may be desirable, for example, to grasp the handles 56 and release the detent 95 so that, having roughly positioned the tube, the cassette can be slid into position with respect to the patient as the arm is rotated back to its operative detent established position shown in FIG. 2a using the adjustability of the slot 47 and arcuate guide 48.

As a further example of the flexibility of the device, the technician may first approach the patient with the cassette carrier folded into the inoperative position, then position the x-ray source 42 and folded arm 50 in very nearly the location at which the radiograph is to be taken. Following this positioning move, the detent 95 can be released, the arm 50 swung away, the carrier dropped into the 90° operative position, then the arm 50 swung back toward the patient to position the cassette.

When the x-radiographic device is intended primarily for use with the film positioning device of the invention, it is desirable to shift the center of gravity of the tube to counterbalance the weight of the positioning device. This may be accomplished by adding an appropriate weight near the top of the x-ray tube, or by shifting the tube mounting point upward with respect to its center of rotation. Of course, the film positioning device is sufficiently light that it can be used as an accessory without counterbalancing.

Figures 3, 4:
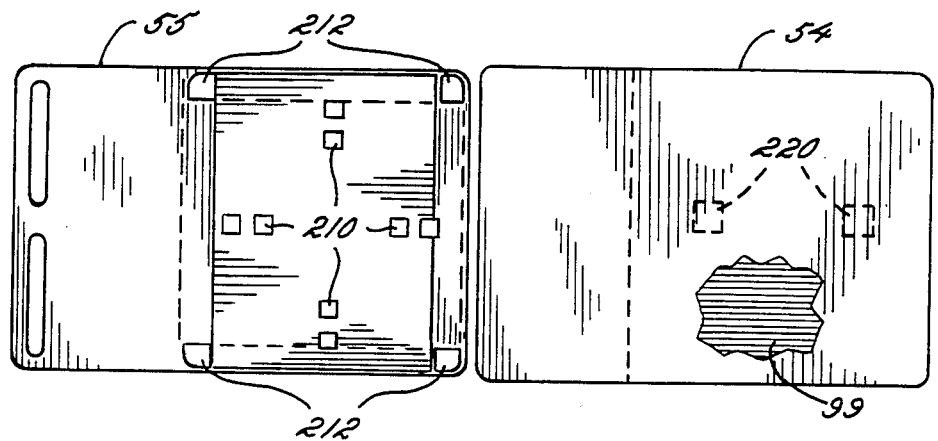
FIG. 3 shows a cassette film drawer and FIG. 4 the holder for the drawer which incorporates a grid, both for use in the embodiment of FIGS. 1 and 2.
Figure 5:
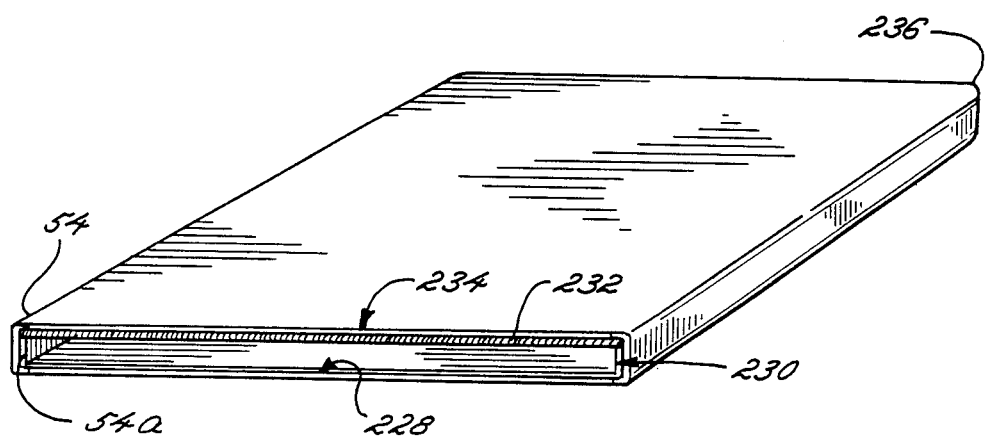
FIG. 5 is a view taken generally along the line 5—5 of FIG. 4 and showing the structure of the cassette drawer holder with focused grid.
Figure 6:
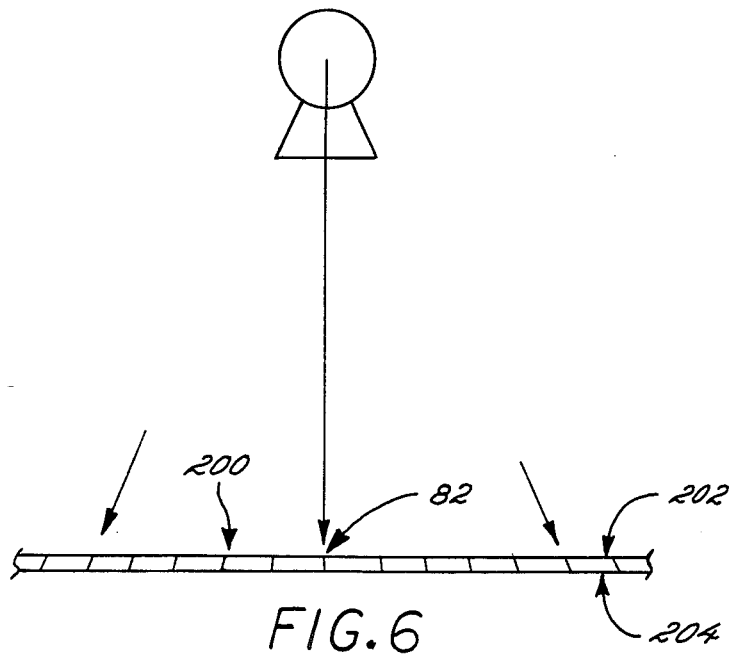
FIG. 6 is a schematic view which illustrates the grid cut-off problem and in exaggerated fashion the nature of the structure of a focused grid.

Turning now to FIGS. 3-5, there is shown additional detail on the cassette drawer, 55 and the holder 54 which receives it. Built into the rightmost portion of the surface of the holder 54 is a focused grid, preferably 17"×17" in dimension. The grid is illustrated in FIG. 4 simply as a series of dashed lines 99. It is well known that the lines represent a series of thin lead slats arranged much like a venetian blind. The slats, made of closely spaced microscopic lead wire, are embedded in aluminum to accurately maintain them in their assigned positions and are thus not visible when viewing the grid surface. However, an exaggerated view is shown in FIG. 6 where the focal spot of the x-ray source 42b is generally indicated at 200 and the focused grid at 202. In the FIG. 6 embodiment, the grid is aligned and thus the rays emanating from the focal spot see only the edge of each slot, and thereby casts a minimum shadow on the x-ray film 204. However, scattered x-rays, for example, those which change direction as they pass through the body being x-rayed, come from directions where they can be absorbed by the grid rather than impinge on the film. It is seen that if the focal spot 82 is moved either left or right the shadow cast by the grid on the film 204 increases with ever-increasing misalignment. That is the condition heretofore referred to as grid cut-off.

Returning to FIGS. 3–5, the drawer 55, preferably made of a suitably rigid plastic material, fits within the holder 54 and is arranged to receive a film cassette to be disposed below the focused grid. For attaching the cassette, fastening means 210 are provided shown in the illustrated embodiment as hook and loop fasteners often sold under the trademark Velcro. The cassette drawer 55 is arranged such that the hook fasteners are positioned at 210 and the loop fasteners are positioned in the corresponding positions on the underside of a conventional film cassette. Positioning means 212, shown in the illustrated embodiment as upstanding blocks, preferably machined from easily worked plastic material such as that sold under the trademark Lucite, are disposed to accurately position the cassette in one of two selectable positions. It is recalled the typical cassette is a 14"×17" rectangle. In the solid line illustration, the edges of the cassette engage the vertical (as illustrated in the drawing) edges of the mounting blocks 212, thereby positioning the longer dimension of the film vertically. Similarly, the cassette can be rotated 90° to engage adjacent sides of the blocks 212 for positioning the longer dimension of the film horizontally (as shown in the drawings). Referring briefly to FIG. 5, there is shown a section of the cassette holder 54 with cassette drawer 54a in position exposing the cassette 228. It is shown that the cassette holder 54 is formed on a steel or alloy frame 230 which, of course, has one open end to receive the drawer 54a. The focused grid as shown at 232 is protected by a Teflon cover 234 which covers all surfaces of the cassette holder. The rear edge 236 can be removed to expose the rear surface of the focused grid 232. It may be desirable to remove the focused grid, in limited circumstances, for at least two reasons. First is to alter the direction of the grid from parallel to perpendicular by rotating it 90°. Secondly, recalling the ability of the disclosed device to utilize a second focal length, it is occasionally necessary to remove, say, the 40" focal length grid to replace it with, say, a 56" focal length grid.

It will now be appreciated that when the cassette is loaded in the cassette drawer and the drawer slipped within the cassette carrier 54 (and with the holder in its operative position), precise alignment is achieved between the elements necessary to consistently secure high quality x-ray images.

As an associated feature of the invention, the arrangement provides for fixedly positioning radiation sensors with respect to the film. The sensors are utilized in conjunction with an automatic exposure device (not shown) which terminates the x-ray exposure when a predetermined amount of x-radiation is sensed. When a separate portable sensor device is used, the variability of position can make automatic exposure less than desirable. If the sensor is placed, for example, behind the spine, the results in the radiograph are much different than if located behind primarily soft tissue.

To avoid the problem of variability of positioning of x-radiation sensors, such sensors are built directly into the holder 54 at the positions illustrated at 220. Using, for example, a pair of sensors whose spacing is significant compared to anatomical differences, it is possible to sum or average the signals as a superior method for utilizing automatic exposure control in a portable x-radiograph. In the preferred embodiments, the sensors 220 are positioned at the rear surface of the cassette holder 54 so as not to interfere with the travel of x-radiation to the film.

In use, the portable x-radiography apparatus is shown in FIG. 1 in the transport position. In that position, a technician transports the portable x-radiography apparatus to the bedside of a patient to be x-rayed. When the mobile x-ray apparatus is moved into position adjacent the bedside, the x-ray head is advanced up the standard 18. Then by rotating the head on the standard 18 and by rotating the head itself on the cross arm, the cassette holder 54 is deployed from the stowed position shown in FIG. 1 to the operative position shown in FIG. 2a. The cassette drawer, 55 is then removed and a cassette installed, and the drawer 55 inserted in the holder 54. At that point, in some cases primarily by manipulating the x-ray source 42 (the latch 70, 80, 81 keeps the surface 48 deployed so that it is fixed in position with respect to the x-ray source), the apparatus is positioned with the x-ray source 42 on one side of the patient and the film holder on the other rigidly aligned with respect thereto. Other variations of alignment have been described above, including use of the handles 52 in obtaining position in more difficult cases. The radiograph is taken and the procedure repeated if additional views are needed. When the session is completed, the cassette carrier 54 is folded back on itself and the head with attached film holder redeployed to the transport position shown in FIG. 1.

Figure 7:
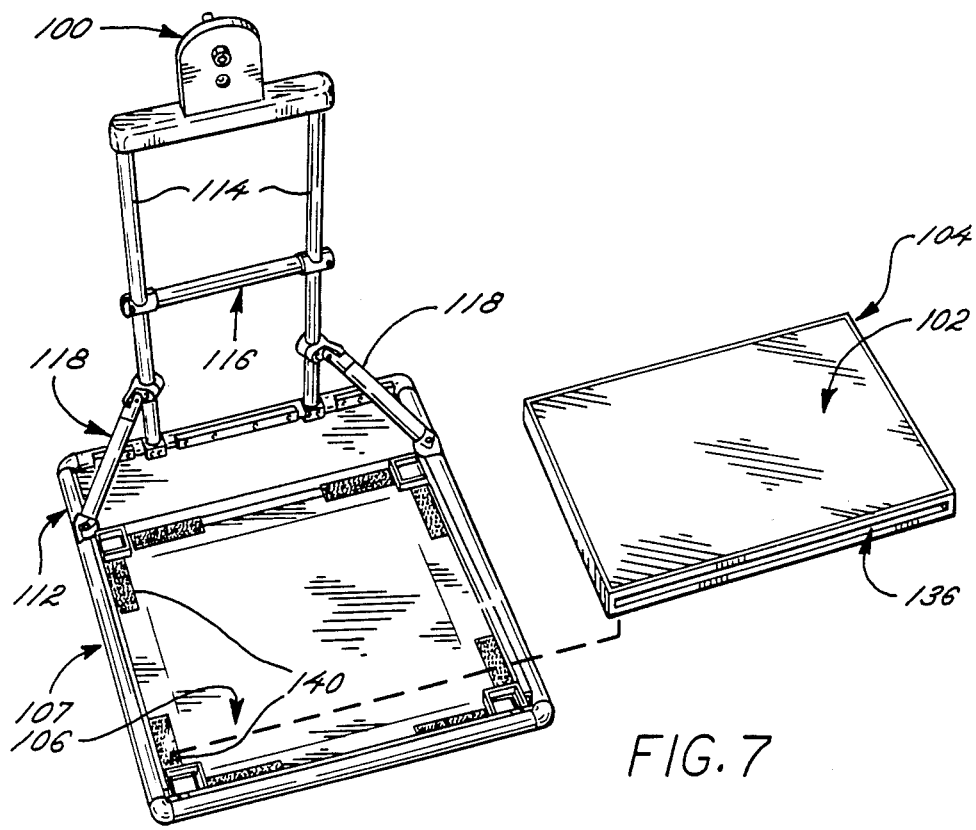
FIG. 7 is a perspective view of a second embodiment of the invention with a nonfolding cassette holder and a removable grid cassette.

Turning now to the alternative embodiment of FIG. 7, there is shown another fixed geometry x-ray exposure device 107. Mounting means 100 are provided which are capable of being affixed in a definite and fixed relationship with an x-ray source 42a (see FIG. 8) and establishing a surface 102 fixed at a predetermined distance from the x-ray source 42a and properly aligned therewith. The surface 102 in this embodiment is carried by a grid cassette 104 which as suggested by the dashed lines, is intended to fit within a rectangular aperture 106 which forms a cassette holder 107.

In contrast to the prior embodiment, the current embodiment sacrifices certain flexibility in being able to pivot the surface 102 with respect to the arm, but in doing so secures a minor amount of additional rigidity. The embodiment is based on a rigid frame 112 which serves, in part, as the cassette holder recess supported from the mounting means 100 by a pair of rods 114 which are crossbraced at 116 and further rigidified with respect to the film-holding frame 112 by a pair of angled support members 118.

The mounting means 100, is secured to an attaching means 119 (see FIG. 8) in the form of a plate 120 rigidly affixed between the x-ray source 42a and the collimator housing 44a. Thus, the entire apparatus is rigidly affixed with respect to the x-ray source 42a and creates, as did the first embodiment, a surface 102 which is at a precise and predetermined position and alignment with respect to the focal spot of the x-ray source 42a.

Figure 8:
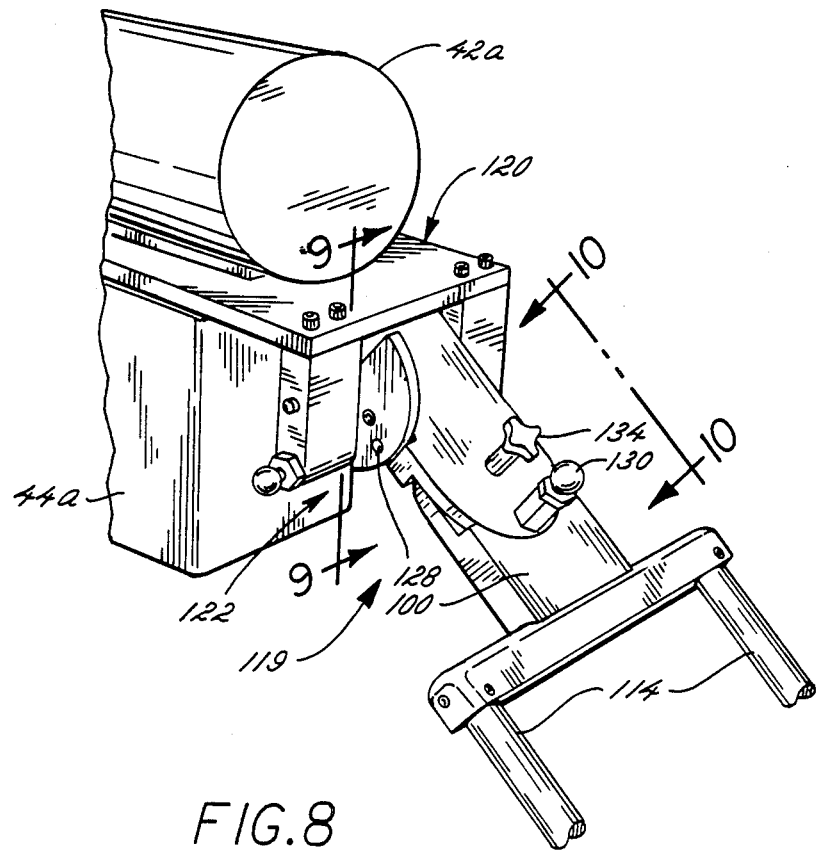
FIG. 8 is a perspective view of means for attaching the apparatus to the x-ray source.
Figure 9:
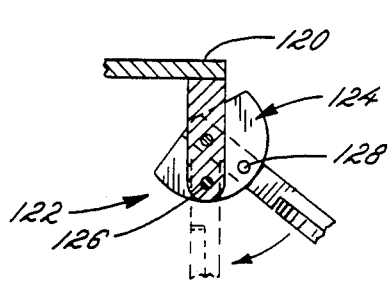
FIG. 9 is a view of the positioning mechanism taken along the line 9—9 of FIG. 8.

For purposes of accurately establishing the focal distance, while allowing some movement of the cassette carrier 107 with respect to the x-ray tube and patient, an attachment means 119 is pivotably and detachably secured to the plate 120. As shown in FIG. 8, a detent means 122 permits the pair of rods 114 to be tilted away from the x-ray tube for allowing approximate positioning of the x-ray tube with respect to the patient without interference from the cassette holder 107. The cassette holder 107 is then pivoted into position, whereupon an aperture 128 in the bracket 124 allows a spring loaded plunger 126 to engage an aperture 128 so that the film plane 102 is locked, not only at the focal distance, but with the grid, which is a part of the cassette 104 of FIG. 7, centered on the focal spot of the beam. FIG. 9 shows in solid line position the rotated position of the arm and holding means whereas the operative fixed location with detent engaged is shown in dashed lines.

Figure 10:
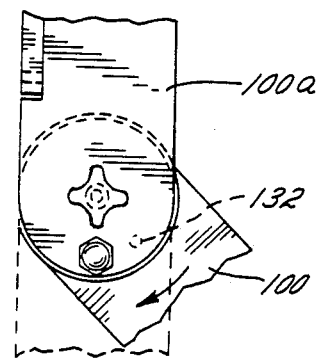
FIG. 10 is a view similar to FIG. 9 taken along the line 10—10 of FIG. 8.

Similarly, as shown in FIG. 8, a further detent means 130 is provided which when disengaged allows the cassette holder 107 (see FIG. 7) to pivot clockwise or counterclockwise with respect to the x-ray source 42a, but which when engaged in the aperture 132 locks the cassette holder 107 in the desired predetermined position with respect to the x-ray source 42a and collimator 44a. FIG. 10 shows in solid lines the unlocked position where the arm is rotated out of position, and in dashed lines the operative position with the detent locked. (Aperture 132 is shown dashed as being in hidden lines in the solid-line unlocked view.) Additionally, a threaded fastener 134 secures the mounting means 100a to the mounting means 100 to allow for quick release of the entire carrier and arm for the purposes previously described.

The apparatus is so constructed and arranged that when the detents 126, 130 are in position, placing the cassette holder 107 in the operative position, the plane of the film 102 is focused on the focal spot of the x-ray source 42a and the grid is aligned with the focal spot such that grid cut-off is not a problem.

In the embodiment of FIG. 7 the grid cassette 104 includes a slot 136 into which is positioned the film cassette. The grid cassette 104 also includes a grid forming the surface 102. The cassette 104 is substantially rectangular, typically 14×17 inches, and can be positioned in the cassette holder 107 either vertically or horizontally. As in the prior embodiment, Lucite blocks 138 and Velcro strips 140 are used not only to position the cassette 104 but also to allow it to be rotated 90° between its vertical or horizontal positions.

The end result, once a cassette is properly positioned and the detents 126, 130 are locked in position, is that the film plane is absolutely perpendicular to the central ray of the x-ray tube and the grid is absolutely centered on that central ray such that radiographs comparable in quality to those produced in the x-ray department can be achieved at bedside.

I claim as my invention:

1. In mobile x-radiography, including a mobile x-ray apparatus which is sufficiently mobile to be brought to bedside for taking radiographs of a body resting on a support, the mobile x-ray apparatus having an x-ray source which is adjustable to a sufficient range of orientations to allow the exposure of radiographs of portions of the body in a plurality of orientations at bedside, the combination with said mobile x-ray apparatus of apparatus for improving the consistency and quality of radiographic images comprising, in combination:

a film cassette for holding an x-ray film to be exposed, holding means for supporting said film cassette configured to be positioned between the body to be radiographed and the body support, focused grid means associated with said holding means for reducing the effects of scattered radiation on the radiographic image, and means connecting the x-ray source and the holding means for establishing a fixed and aligned relationship between the x-ray source, the grid and the film cassette, and a predetermined focal distance between the x-ray source and film cassette during an x-ray exposure; the connecting means including physical link means between the x-ray source and holding means for positioning the holding means between the body and its support in alignment with the x-ray source during adjustment thereof to maintain said fixed and aligned relationship as the x-ray source is adjusted within its range of orientations.

2. The combination as set forth in claim 1 in which the focused grid is in a grid cassette into which the film cassette is inserted, the holding means having positioning means for accurately locating the grid cassette with respect to said holding means.

3. The combination as set forth in claim 1 in which the holding means comprises a cassette holder for receiving the film cassette, the focused grid being constructed as a part of the cassette holder in predetermined alignment with the x-ray source.

4. The combination as set forth in claim 1 in which the connecting means includes a physical arm having mounting means for connection to the x-ray source for assuring precise physical positioning with respect to the x-ray source, the holding means including a cassette holder connected to the arm in a predetermined position and orientation to establish said fixed and aligned relationship.

5. The combination as set forth in claim 4 wherein the cassette holder is fixably mounted with respect to said arm.

6. The combination as set forth in claim 4 including a hinge means connecting the cassette holder to the arm and allowing pivoting of the cassette holder between a retracted position and a deployed position which establishes said fixed and aligned relationship and lock means for securing the cassette holder in the deployed position.

7. The combination as set forth in claim 6 including a detachable coupling associated with said hinge means for releasing the cassette holder from the arm.

8. The combination as set forth in claim 6 wherein said cassette holder and said arm have mating surfaces which, when abutted, establish said fixed and aligned relationship.

9. The combination as set forth in claim 8 including handle means at the lower end of the arm for facilitating maneuvering thereof, said handle means including a buttressed portion forming one of said mating surfaces.

10. The combination as set forth in claim 4 including detachable coupling means for releasably securing said arm to the mounting means.

11. The combination as set forth in claim 4 wherein the mounting means for connection to the x-ray source includes pivotable means for pivoting said arm into and out of a deployed position, and detent means for establishing said fixed and aligned relationship when the arm is in the deployed position.

12. The combination as set forth in claim 4 wherein the mounting means for connection to the x-ray source includes a mounting plate disposed between the x-ray source and an associated collimator.

13. The combination as set forth in claim 4 wherein there is associated with the arm telescoping means for altering the distance between the x-ray source, the grid and the film cassette, at least two detent means for establishing two predetermined focus to film distances, said combination further including interchangeable focused grids for the two different focus to film distances.

14. In mobile x-radiography, including a mobile x-ray apparatus which is sufficiently mobile to be brought to bedside for taking radiographs of a body resting on a support, the mobile x-ray apparatus having an x-ray source which is adjustable to a sufficient range of orientations to allow the exposure of radiographs of portions of the body in a plurality of orientations at bedside, the combination with said mobile x-ray apparatus of a film positioning and alignment device comprising in combination:

means for providing a mounting surface connected to the adjustable x-ray source and having a predetermined location with respect to the focal spot of the x-ray source, a positioning arm of predetermined length coupled to the mounting surface, means for holding a film cassette containing an x-ray film, the holding means being sufficiently thin to allow positioning thereof between the body to be radiographed and the body support, means for associating a focused grid with the film cassette, means for attaching the holding means to the positioning arm the attaching means being constructed and arranged as to allow holding means to be positioned between the body to be radiographed and the body support as the x-ray source is adjusted for taking a radiograph, and means for establishing the spatial relationship between the holding means and the attaching means to secure precise alignment and position of the grid and film cassette with respect to the x-ray source within its range of orientations.

15. The combination as set forth in claim 14 wherein the means for establishing the spatial relationship includes fixed brace means for connecting the positioning arm and the attaching means in precise relationship to secure said precise alignment and position.

16. The combination as set forth in claim 14 in which the means for establishing the spatial relationship includes hinge means for attaching the holding means to the positioning arm such that the holding means can pivot with respect to said arm, the means for establishing the spatial relationship further including means for defining and holding the hinge position which establishes said precise alignment and position.

* * * * *